US00PP25007P3

(12) United States Plant Patent
De Wit et al.

(10) Patent No.: US PP25,007 P3
(45) Date of Patent: Oct. 28, 2014

(54) APPLE TREE NAMED 'ASFARI'

(50) Latin Name: ***Malus domestica* Borkh.**
Varietal Denomination: ASFARI

(71) Applicant: Better3fruit, N.V., Heverlee (BE)

(72) Inventors: Inge De Wit, Lovenjoel (BE); Hendrik Eyssen, Holsbeek (BE); Johan Keulemans, Korbeek-Lo (BE); Johan Nicolaï, Sint-Truiden (BE); Els Pauwels, Amougies (BE); Paul Van Laer, Heks (BE)

(73) Assignee: Better3Fruit, N.V., Heverlee (BE)

( * ) Notice: Subject to any disclaimer, the term of this patent is extended or adjusted under 35 U.S.C. 154(b) by 4 days.

(21) Appl. No.: 13/694,826

(22) Filed: Jan. 9, 2013

(65) Prior Publication Data

US 2013/0185833 P1 Jul. 18, 2013

(30) Foreign Application Priority Data

Jan. 16, 2012 (QZ) ..... PBR 20120099

(51) Int. Cl.
*A01H 5/00* (2006.01)

(52) U.S. Cl.
USPC ..... Plt./172

(58) Field of Classification Search
USPC ..... Plt./172
See application file for complete search history.

*Primary Examiner* — Anne Grunberg
(74) *Attorney, Agent, or Firm* — Foley & Lardner LLP

(57) ABSTRACT

A new and distinct variety of *Malus domestica* apple tree named 'Asfari', particularly characterized by early maturity of fruit, yellow fruit over color, sometimes with a slight pink blush; good storability of fruit for its harvest date; aromatic and sweet flavor; and clean skin.

9 Drawing Sheets

Figure 1:
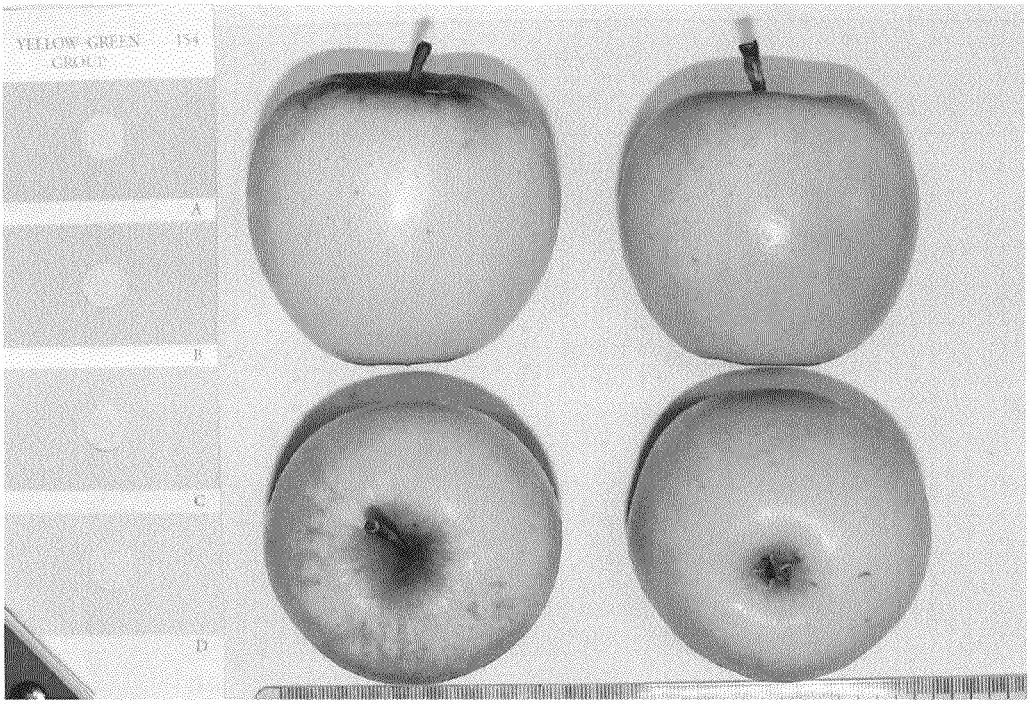

Latin name of the genus and species of the plant claimed: *Malus domestica* Borkh.

Variety denomination: 'ASFARI'.

PRIORITY CLAIM

This application claims priority under 35 U.S.C. §119(f) of the Community plant variety office (CPVO) application No. 2012/0099 filed Jan. 16, 2012.

BACKGROUND OF THE INVENTION

The present invention relates to a new and distinct variety of Apple tree, botanically known as *Malus domestica* Borkh. of the Rosaceae family, and hereinafter referred to by the variety denomination 'ASFARI'.

The new *Malus* variety is a product of a controlled breeding program conducted by the inventor(s), Inge De Wit, Hendrik Eyssen, Johan Keulemans, Johan Nicolaï, Els Pauwels and Paul Van Laer, in Rillaar, Belgium. The objective of the breeding program was to develop a new *Malus* variety with crisp and juicy flesh, as well as good storage capacity and shelf life.

The new *Malus* variety originated from a cross made by the inventor(s) in 1997 in Belgium. The female or seed parent is the *Malus domestica* variety designated 'ELSTAR' (patented, U.S. Plant Pat. No. 6,450 and Plant Breeder's Rights Nos.: BE 90002, DE APF 00007, FR 10412, GB 900030 and NL APP0060). The male or pollen parent is the *Malus domestica* variety designated 'DELCORF' (registered, Plant Breeder's Rights No. FR 112364). The new *Malus* variety was discovered and selected by the inventors within the progeny of the stated cross in a controlled environment in 2003 in Rillaar, Belgium.

Asexual reproduction of the new *Malus* variety by grafting onto rootstocks was first performed in the winter of 2003-2004 in Belgium, and has demonstrated that the combination of characteristics as herein disclosed for the new variety are firmly fixed and retained through successive generations of asexual reproduction. The new variety reproduces true to type.

BRIEF DESCRIPTION OF THE INVENTION

The following traits have been repeatedly observed and are determined to be unique characteristics of 'ASFARI' which in combination distinguish this Apple tree as a new and distinct variety:

1. early maturity of fruit;
2. yellow fruit overcolor, sometimes with a slight pink blush;
3. good storability of fruit for its harvest date;
4. aromatic and sweet flavor; and
5. clean skin.

In comparison to the parental varieties, 'ELSTAR' and 'DELCORF', 'ASFARI' differs primarily in the traits listed in Table 1.

TABLE 1

Comparison with Parental Varieties

| Trait | New Variety 'ASFARI' | Female Parent 'ELSTAR' | Male Parent 'DELCORF' |
|---|---|---|---|
| Fruit: over color | None or slight pink blush | Red | Red |
| Fruit: pattern of over color | Solid | Flushed and mottled | weakly defined flush with strongly defined stripes |
| Fruit: taste | Sweet | Sour | Sour-sweet |
| Fruit: time for harvest | 3 weeks before Elstar | — | 2 weeks before Elstar |

Of the many commercial varieties known to the present inventor(s), the most similar in comparison to the new *Malus* variety 'ASFARI' is the *Malus* variety 'GOLDEN DELICIOUS' (unpatented), in the following characteristics described in Table 2:

TABLE 2

| Comparison with Similar Variety | | |
|---|---|---|
| Characteristic | New Variety 'ASFARI' | Comparison Variety 'GOLDEN DELICIOUS' |
| fruit: time for harvest | early to medium (5 weeks before Golden) | late |
| fruit: time of eating maturity | early to medium | late |
| fruit: ground colour | yellow | yellow green |

BRIEF DESCRIPTION OF THE PHOTOGRAPHS

The accompanying photographs illustrate the overall appearance of the new *Malus* variety 'ASFARI' showing the colors as true as is reasonably possible with colored reproductions of this type. Colors in the photographs may differ slightly from the color values cited in the detailed botanical description, which accurately describe the color of 'ASFARI'.

FIG. 1—shows a close-up view (side, top and bottom) of mature fruit of 'ASFARI'.

Figure 2:
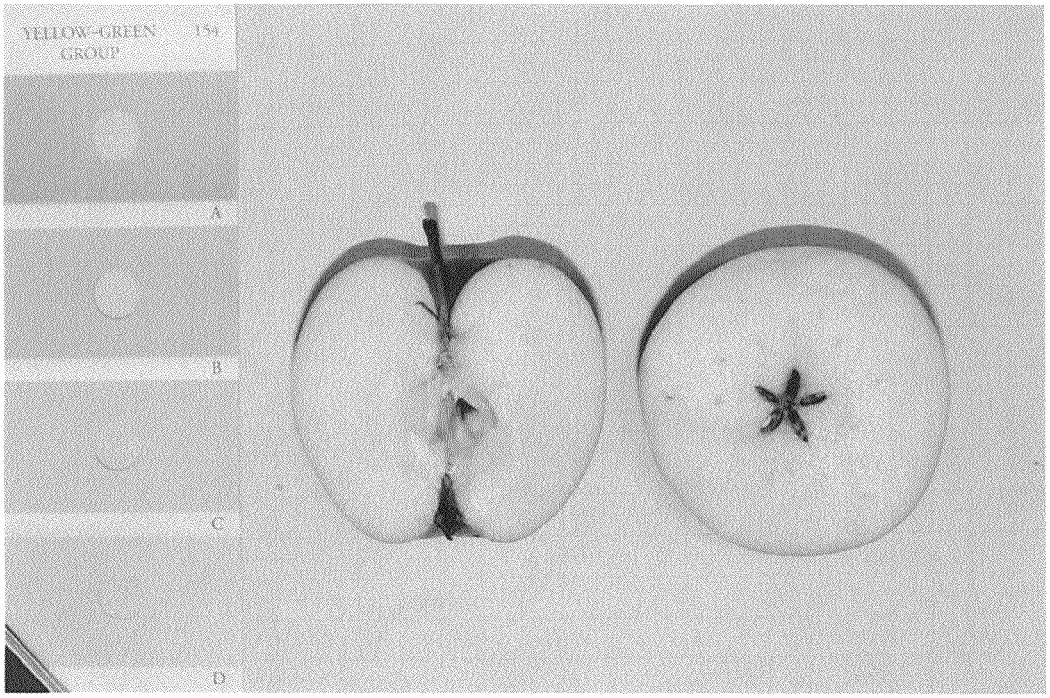

FIG. 2—shows dissection views of mature fruit of 'ASFARI'.

Figure 3:
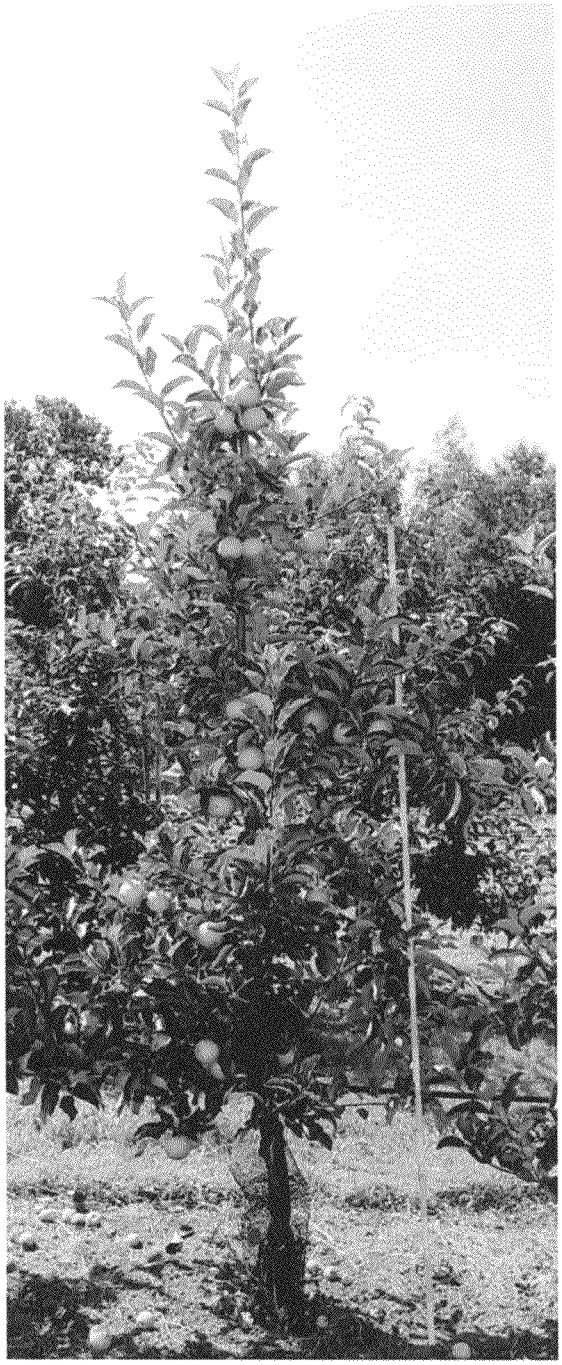

FIG. 3—shows a fruit-bearing tree of 'ASFARI', at 6 years of age.

Figure 4:
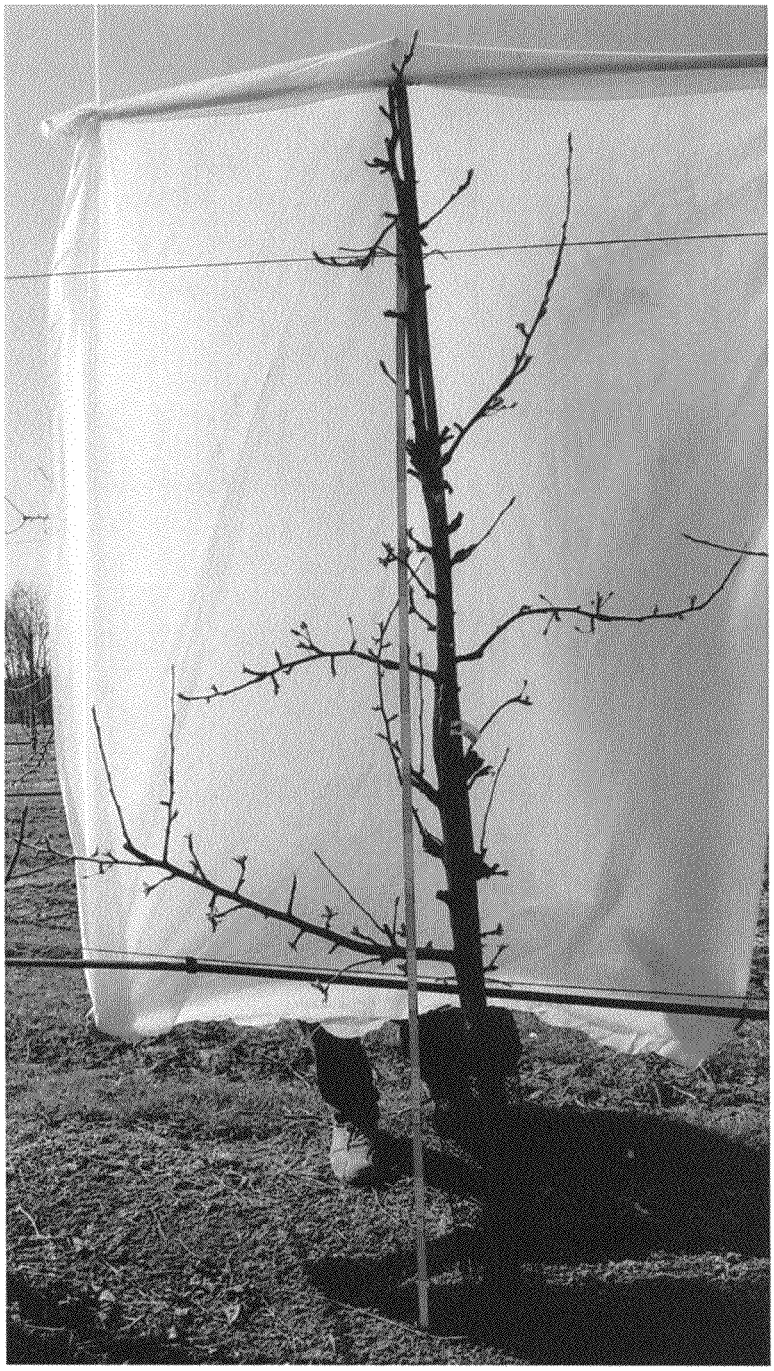

FIG. 4—shows a dormant tree of 'ASFARI', at 6 years of age

Figure 5:
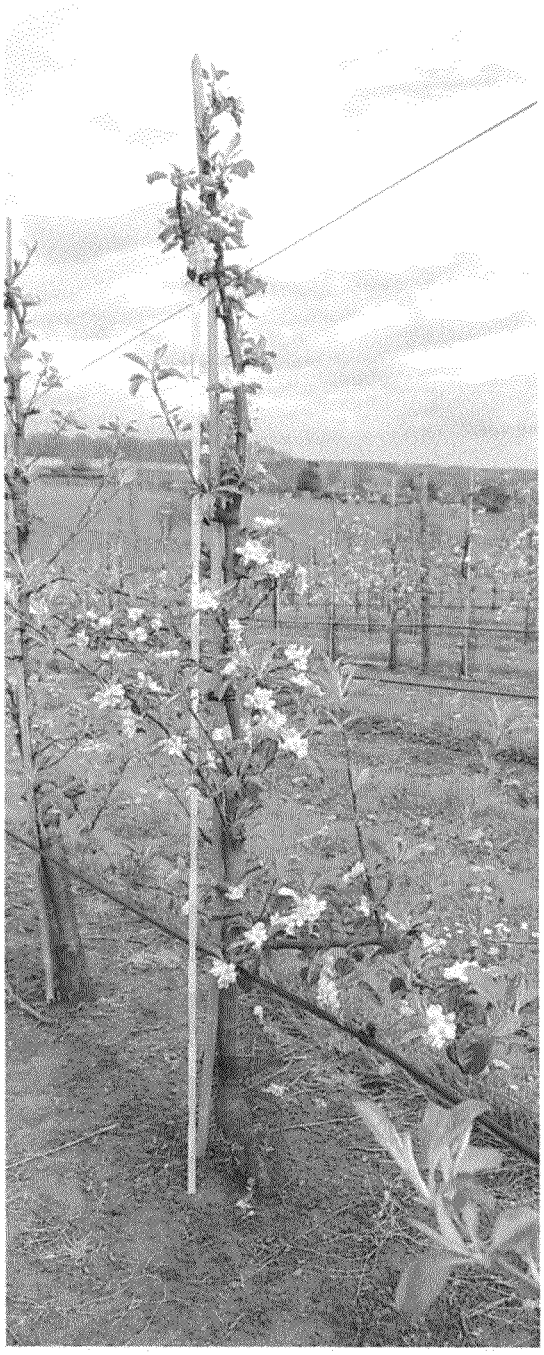

FIG. 5—shows a blooming tree of 'ASFARI', at 6 years of age.

Figure 6:
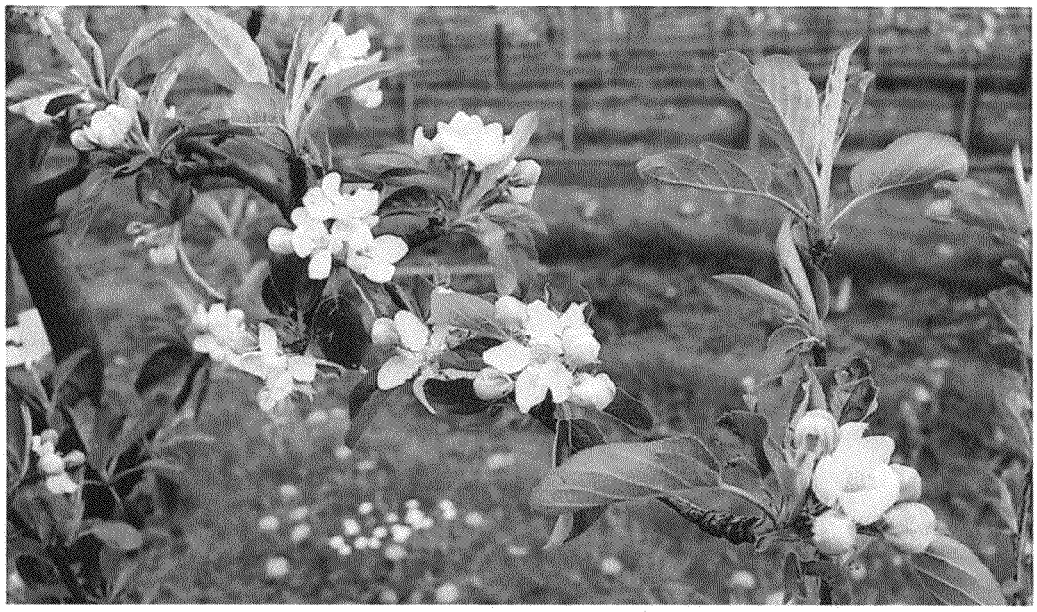

FIG. 6—shows inflorescence of 'ASFARI'.

Figure 7:
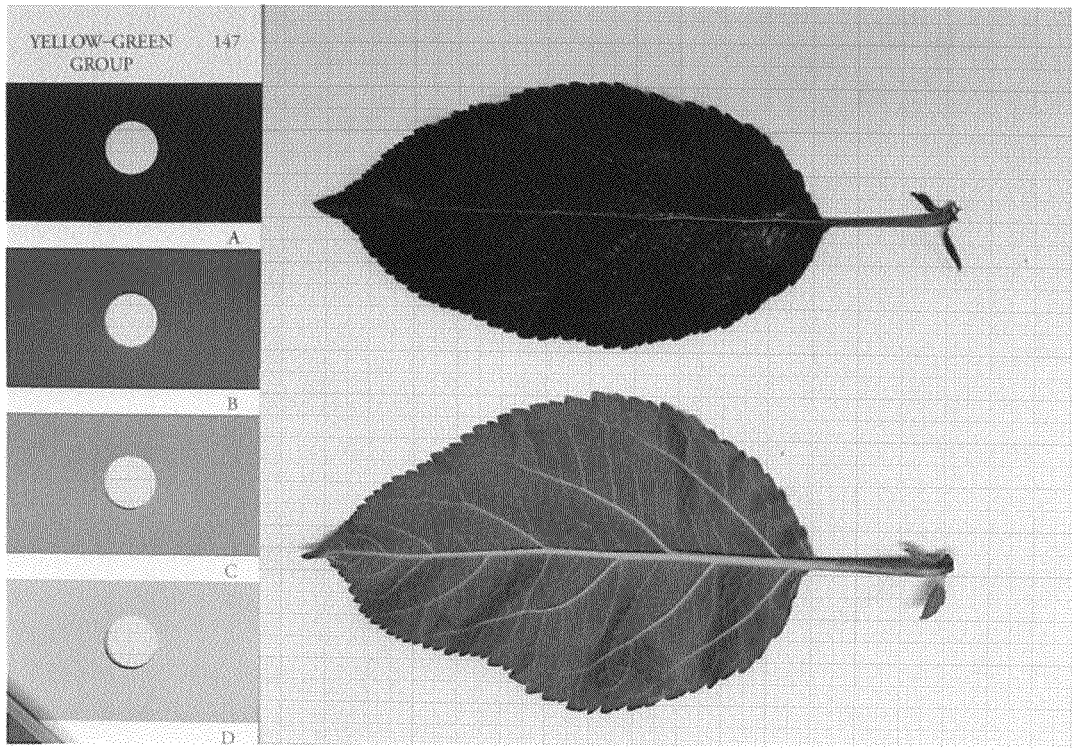

FIG. 7—shows the upper surface (top) and under surface (bottom) view of leaves of 'ASFARI'.

Figure 8:
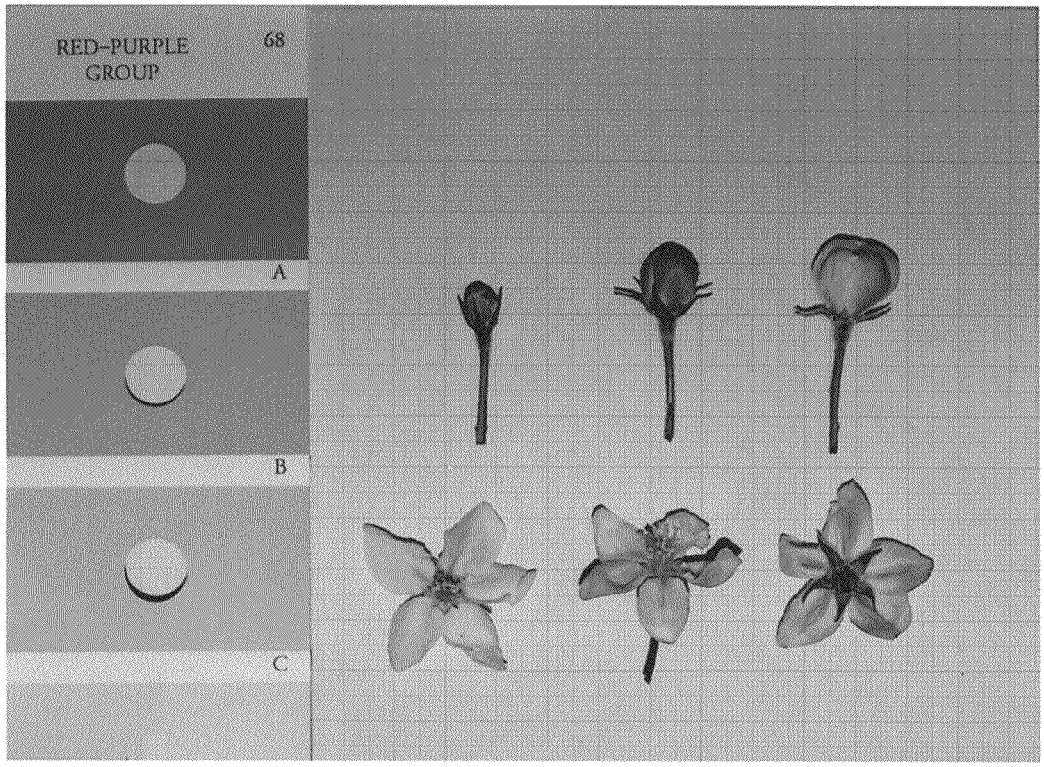

FIG. 8—shows different stages of development of the flowers and the (from left to right) top, side and bottom view of a fully expanded flower of 'ASFARI'.

Figure 9:
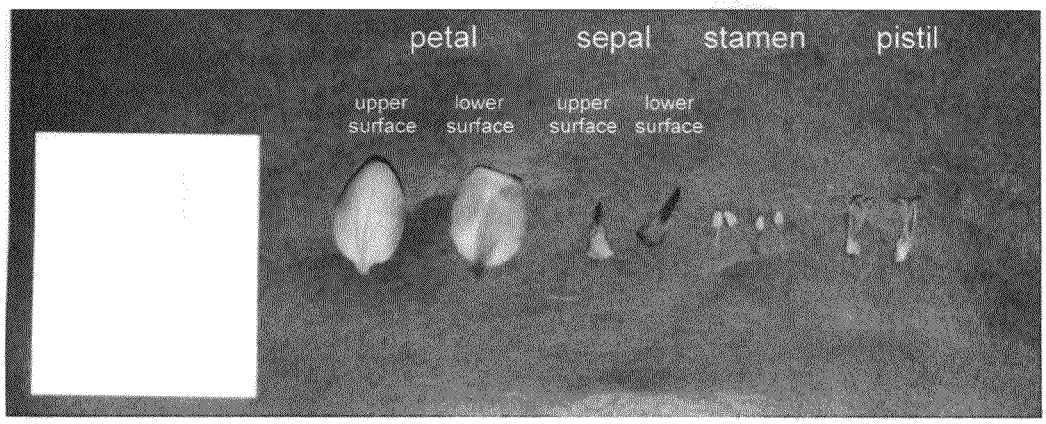

FIG. 9—shows different parts of a flower of 'ASFARI'.

DETAILED BOTANICAL DESCRIPTION

The new *Malus* variety 'ASFARI' has not been observed under all possible environmental conditions. The phenotype of the new variety may vary with variations in environment such as temperature, light intensity, and day length without any change in the genotype of the Apple tree.

The aforementioned photographs, together with the following observations, measurements and values describe trees of 'ASFARI' as in Rillaar, Belgium, under conditions which closely approximate those generally used in commercial practice.

Unless otherwise stated, the detailed botanical description includes observations, measurements and values based on 6 year old 'ASFARI' trees grown in Rillaar, Belgium from 2007 to 2012. Quantified measurements are expressed as an average of measurements taken from a number of trees of 'ASFARI'. The measurements of any individual tree, or any group of trees, of the new variety may vary from the stated average.

Color references are made to The Royal Horticultural Society Colour Chart (R.H.S.), ($4^{th}$ edition, 2001), except where general colors of ordinary significance are used. Color values were taken under daylight conditions.

All of the trees of 'ASFARI', insofar as they have been observed, have been identical in all the characteristics described below.

Classification:

*Botanical.*—*Malus domestica.*

Parentage:

*Female or seed parent.*—*Malus* variety designated 'ELSTAR' (patented).

*Male or pollen parent.*—*Malus* variety designated 'DELCORF' (registered).

Propagation: Grafting onto rootstocks.

Growing conditions:

*Light intensities.*—Full sunlight.

*Temperature.*—During day, grown in range of 2° C. to 23° C., and during evening, grown in range of −5° C. to 13° C. (based on average month temperature).

Tree:

*Age.*—Observed trees were 6 years old.

*Vigor.*—Weak vigor.

*Form.*—Upright — spreading.

*Habit.*—A medium-sized tree with one trunk and about 6+/−1 leaders; main branches spreading; crown symmetrical.

*Branching habit.*—Main branches angle is about 74+/−10° with respect to trunk if allowed to grow naturally.

*Density.*—About 2200 trees per hectare.

*Cropping behavior.*—Normal beginning production, good and constant productivity, regular flowering, no biennial bearing.

*Type of bearing.*—Spurs and long shoots.

*Production.*—About 13.8 kg/tree in 2012.

*Size at maturity.*—Height: About 244+/−8 cm. Spread: About 156+/−22 cm.

*Trunk.*—Height (up to leaders): About 71+/−8 cm. Diameter: About 47+/−6 mm. Texture: Slightly rough. Bark color: Primarily RHS 197B, with RHS 199A, underbark. Trunk Lenticels: Length: About 1.2+/−0.1 mm. Width: About 4.4+/−0.7 mm. Color: RHS 167C. Density: About 1.8+/−0.4 per $cm^2$.

*Branches.*—Number per tree: About 15+/−3. Length: Maximum of 85+/−13 cm; minimum of 3+/−1 cm. Diameter (at 2 years): About 11+/−3 mm. Surface texture: Slightly rough. Pubescence: Little. Color: Mature (after about 3 years old): RHS N199B. New Growth: RHS 200B. Internode length: About 3+/−1 cm. Internode diameter: About 11+/−3 mm. Branch lenticels: Length: About 1.5+/−0.4 mm. Width: About 1.7+/−0.4 mm. Color: RHS 161A. Density: About 4.7+/−1.3 per $cm^2$.

*Spur.*—Present: Yes. Distance between each spur: On the 2 and 3 year old branches, the distance is about 3+/−1 cm. Diameter of each spur: About 6+/−1 mm. Number of fruit per spur: About 0.8+/−0.8.

Foliage:

*Arrangement.*—Alternate, simple, petiolated.

*Lamina.*—Size: Length: About 109+/−20 mm (fully expanded leaf). Width: About 57+/−8 mm (fully expanded leaf). Length/width ratio: About 1.9+/−0.5. Overall Shape: Ovate, petiolated. Base shape: Cunate. Apex shape: Acute. Margin: Biserrate. Texture: Upper surface: Smooth, glabrous. Under surface:

Medium pubescence. Attitude in relation to shoot: Upwards. Color (mature leaves): Upper surface: RHS 147A. Under surface: RHS 138B. Color (immature leaves): Upper surface: RHS 143C. Under surface: RHS 138C.

*Venation*.—Type: Pinnate venation from central vein to the leaf edge. Color: RHS 144C.

*Petiole*.—Length: About 30+/−6 mm. Diameter: About 1.7+/−0.4 mm. Texture: High pubescence. Color: RHS 144B (upper), RHS 144C (lower), RHS 60A (at the petiole base; upper and lower surfaces).

*Stipule*.—Arrangement: Free standing. Length (distance of stipules from basal attachment of petiole): About 9.9+/−3.4 mm. Width: About 3.1+/−1.2 mm.

Inflorescence:

*Blooming time*.—Medium (similar to Gala and Braeburn).

*Blooming period*.—About 1 week.

*Fragrance*.—Slight.

*Type*.—Corymb.

*Number of flowers per inflorescence*.—About 5.2+/−0.7.

*Inflorescence size*.—Diameter: About 65+/−6 mm. Depth: About 48+/−5 mm.

*Buds*.—Terminal Buds: Number per spur: About 1. Shape: Pointy, triangular. Length: About 9.3+/−1.5 mm. Width: About 4.9+/−0.5 mm. Texture: Smooth, slight pubescence. Color: Apex RHS 200A, and base RHS 183A. Scales: Number: About 5.1+/−0.8. Overall shape: Triangular, folded double around bud. Apex shape: Acuminate. Base shape: Straight, fully grown together at base. Color: Upper: RHS 183A. Lower: RHS N144D. Lateral Buds: Number per spur: About 0.1+/−0.2. Shape: Pointy, triangular. Length: About 4.6+/−1.2 mm. Width: About 3.3+/−0.5 mm. Texture: Smooth, slight pubescence at apex. Color: Apex RHS 200A, and base RHS 144C. Scales: Number: About 5.0+/−0.6. Overall shape: Triangular, folded double around bud. Apex shape: Acuminate or 3 blunt points. Base shape: Straight, fully grown together at base. Color: Upper: RHS 200B. Lower: RHS 144C.

*Petals*.—Arrangement: Intermediate. Number per flower: 5. Size: Length: About 17+/−1 mm. Width: About 12+/−1 mm. Length/width ratio: About 1.5+/−0.1. Overall shape: Ovate. Apex shape: Obtuse. Base shape: Rounded. Texture (upper surface): Smooth. Texture (lower surface): Smooth. Margin: Entire. Color (upper surface): Apex, RHS 68C, and base, RHS 69D. Color (lower surface): Apex, RHS 68B, and base, RHS 69D.

*Sepals*.—Number per flower: 5. Size: Length: About 9+/−1 mm. Width: About 3.8+/−0.4 mm. Length/width ratio: About 2.3+/−0.2. Overall shape: Triangular. Apex shape: Acuminate. Base shape: Truncate. Texture (upper surface): Smooth, slightly hairy. Texture (lower surface): Smooth, hairy. Margin: Entire. Color (upper surface): Apex, RHS 183A, and base, RHS 143B. Color (lower surface): Apex, RHS 183A, and base, RHS 143B.

*Pedicel*.—Length: About 23+/−4 mm. Diameter: About 1.4+/−0.2 mm. Texture: Smooth, slight hairy (white hairs). Color: RHS 144A.

Fruit:

*Keeping quality*.—The fruit keeps good for an early variety. It can be stored in cold temperature conditions for minimum 8 weeks. It has a shelf life of minimum 1 week.

*Maturity when described*.—1 month after harvest.

*Maturity period after full bloom*.—About 3.5 months after full bloom.

*Date of first and last picking* (*harvest*).—About second and third week of August.

*Type*.—Pome.

*General shape*.—Globose.

*Average weight*.—About 147+/−19 g.

*Fruit size*.—Average height: About 62+/−4 mm. Average diameter (at widest point): About 68+/−3 mm. Position of maximum diameter: ½ of height. Height/thickness ratio: About 0.9+/−0.1.

*Stem*.—Length: About 18+/−4 mm. Diameter: About 2.8+/−0.7 mm. Color: RHS N144C, RHS N199D and RHS N34C.

*Stalk cavity*.—Depth: About 8.3+/−2.2 mm. Width: About 28.3+/−1.9 mm.

*Eye basin*.—Depth: About 5.4+/−1.3 mm. Width: About 23.5+/−2.5 mm. Crowning at calyx end: Weak. Position of sepals: Closed. Calyx tube: Partly open.

*Skin*.—Thickness: 0.4+/−0.1 mm. Texture: Slightly tough. Bloom: Absent. Greasiness: Absent. Firmness (at picking time): 7.1+/−0.6 kg/cm$^2$. Overcolor Color: RHS 179C. Percentage of skin surface with overcolor color: Absent or very small. Pattern of overcolor: Only solid flush. Intensity of overcolor: Low. Ground color: RHS 154D. Skin Lenticels: Length: About 0.6+/−0.2 mm. Width: About 0.4+/−0.1 mm. Color: RHS 152D. Density: About 5.8+/−2.0 n° per cm$^2$.

*Flesh*.—Color: RHS 150D. Texture: Juicy, medium crispy, medium firm, dense. Aroma: Medium. Eating quality: Excellent texture and very good taste. Firmness (at picking time): About 7.6+/−0.3 kg/cm$^2$. Sugar content (at picking time): About 12.1+/−0.8% Brix. Acidity (at picking time): About 7.9+/−0.3 g/l malic acid. Core: Symmetry of core: Overall round, but not all vascular bundles are in the circle. Distinctness of core lines: Weak. Locules: Number (per fruit): 5. Length: About 9+/−2 mm. Width: About 4+/−1 mm. Form: Teardrop form; closed or slightly open.

Seeds:

*Number per fruit*.—About 6.8+/−2.0.

*Number per locule*.—About 1.5+/−0.5.

*Shape*.—Teardrop form.

*Length*.—About 9.9+/−0.7 mm.

*Width*.—About 4.7+/−0.4 mm.

*Texture*.—Smooth.

*Color*.—RHS 165A.

Reproductive organs:

*Androecium*.—Stamen: Number per flower: 20. Length: About 6.4+/−1.4 mm. Anther: Length: About 2.2+/−0.3 mm. Color: RHS 4B. Filaments: Length: About 5.0+/−1.1 mm. Color: RHS 155B. Pollen: Amount: Moderate. Color: RHS 5C. Pollination Requirements: Cross pollination.

*Gynoecium*.—Pistils: Quantity: 5. Length: About 9.5+/−0.9 mm. Color: RHS 144C. Stigmas: Width: About 0.6+/−0.1 mm. Color: RHS N144A. Ovary: Length:

About 3.6+/−0.7 mm. Width: About 1.1+/−0.3 mm. Color: RHS 144C.

Use: Fresh market.

Disease/pest resistance: No known disease or pest resistance.

Disease/pest susceptibility: Low susceptibility to powdery mildew.

Winter hardiness: Tolerant to temperatures down to minimum −10° C. without observed damage to wood and buds of dormant Apple trees.

Drought/heat tolerance: Tolerant to temperatures up to minimum 40° C., growth is limited by drought periods without irrigation.

Shipping/storage characteristics: Sensitive to bruising; good storability under ULO-conditions for minimum 3 months.

We claim:

1. A new and distinct variety of *Malus domestica* apple tree named 'Asfari', as illustrated and described herein.

* * * * *